(12) United States Patent
Zhou

(10) Patent No.: US 11,731,959 B2
(45) Date of Patent: Aug. 22, 2023

(54) TROXACITABINE SYNTHESIS AND CRYSTAL FORM THEREOF

(71) Applicants: BEIJING HEBABIZ BIOTECHNOLOGY CO., LTD., Beijing (CN); GUANGXI HEBABIZ PHARMACEUTICAL TECHNOLOGY CO.,LTD., Guangxi (CN)

(72) Inventor: James Zhou, Westport, CT (US)

(73) Assignees: BEIJING HEBABIZ BIOTECHNOLOGY CO., INC., Beijing (CN); GUANGXI HEBABIZ PHARMACEUTICAL TECHNOLOGY CO., LTD., Guangxi (CN)

( * ) Notice: Subject to any disclaimer, the term of this patent is extended or adjusted under 35 U.S.C. 154(b) by 586 days.

(21) Appl. No.: 15/755,130

(22) PCT Filed: Apr. 18, 2016

(86) PCT No.: PCT/CN2016/079606
§ 371 (c)(1),
(2) Date: Feb. 26, 2018

(87) PCT Pub. No.: WO2017/031994
PCT Pub. Date: Mar. 2, 2017

(65) Prior Publication Data
US 2020/0247787 A1    Aug. 6, 2020

(30) Foreign Application Priority Data

Aug. 26, 2015 (CN) .......................... 201510529276.3
Aug. 27, 2015 (CN) .......................... 201510534020.1

(51) Int. Cl.
*C07D 405/04* (2006.01)

(52) U.S. Cl.
CPC ........ *C07D 405/04* (2013.01); *C07B 2200/13* (2013.01)

(58) Field of Classification Search
CPC .. C07D 405/04; C07B 2200/13; A61K 31/506
See application file for complete search history.

(56) References Cited

FOREIGN PATENT DOCUMENTS

| CN | 105503838 A | 4/2016 |
|---|---|---|
| WO | 0158894 A1 | 8/2001 |
| WO | 03062229 A1 | 7/2003 |

OTHER PUBLICATIONS

Leonard, John Lygo, Barry Procter, Garry. (2013). Advanced Practical Organic Chemistry (3rd Edition). Taylor & Francis (Year: 2013).*
International search report for patent application No. PCT/CN2016/079606 dated Jul. 7, 2016.

* cited by examiner

*Primary Examiner* — Yong S. Chong
(74) *Attorney, Agent, or Firm* — Bachman & LaPointe, P.C.

(57) ABSTRACT

This invention provides synthesis method, crystallization method, etc. for troxacitabine, and also the crystal form and use of troxacitabine.

8 Claims, 5 Drawing Sheets

TROXACITABINE SYNTHESIS AND CRYSTAL FORM THEREOF

TECHNICAL AREA

This invention falls under the scope of pharmacochemistry. To be more specific, this invention involves the synthesis methods, crystal forms, etc of troxacitabine.

BACKGROUND TECHNOLOGIES

Troxacitabine(4-amino-1-[(2S,4S)-2-(hydroxymethyl)-1,3-dioxol-4-yl] pyrimidine-2-Ketone, Troxacitabine, Troxatyl™) is an antitumor cytidine analogue developed by Yale University, USA. In phases I/II clinical studies performed in the USA using various dosing regimens for many years, troxacitabine was administered alone or in combination with other chemotherapeutic agents for the treatment of multiple solid tumors or blood malignancy in 825 patients. In particular, troxacitabine also has anti-hepatitis B virus and anti-HCC effects.

The synthesis method of troxacitabine was disclosed in the Chinese patent application (No. 201310275643.2). In this method, dyhydroxy L-menthyl acetate is used as starting materials to condensation react with glycolic aldehyde and derive halides after its hydroxy being halogeneated. Halides couple with cytosine to derive a conjugate that is reduced to derive troxacitabine. However, as discovered by the innovator of this invention, this method is associated with a time-consuming and complicated procedure since condensation, halogenation, coupling and reduction are involved in different reaction systems. In particular, intermediate products occur in this method, which require frequent changing of reaction container as a result of multiple separations and are unsuitable for scaling up. Therefore, this method is not very suitable for commercial production.

After long-term study and experiment, the innovator of this invention has established a easy-to-perform synthesis method that allows for derivation of troxacitabine using two steps of reaction only and is in particular suitable for scale up and thereby highly suitable for commercial production. To be more surprising, the products derived by this synthesis method (in particular through refining and purification) gave the innovator a hint that multiple crystal forms may be present. To this end, the innovator has conducted deep study, which successfully derived multiple crystal forms of troxacitabine, in particular the crystal forms that is easier to be promoted due to its good stability under room temperature and room humidity.

Overview of Invention

This invention provides the synthesis method and crystal forms of troxacitabine, as well as the crystallization method and use of the crystal forms.

Highlight 1: Specifically speaking, this invention provides the synthesis method of formula III compound using the synthesis reaction formula described below:

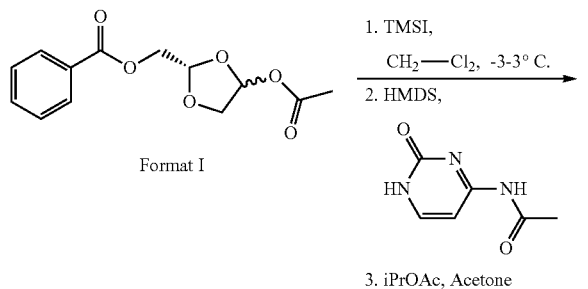

Format I

1. TMSI, $CH_2-Cl_2$, -3-3° C.
2. HMDS,
3. iPrOAc, Acetone

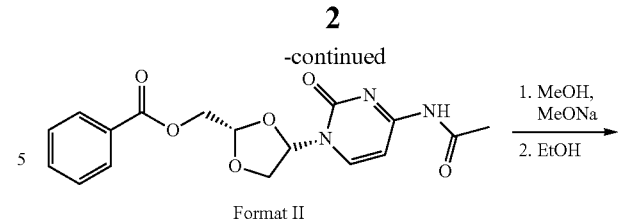

Format II

1. MeOH, MeONa
2. EtOH

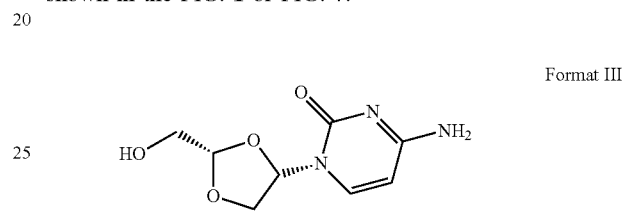

Format III

Highlight 2: this invention provides the crystal form of formula III compound (crystal form A). The crystal form has a basically identical X-ray powder diffractogram to that shown in the FIG. 1 or FIG. 7.

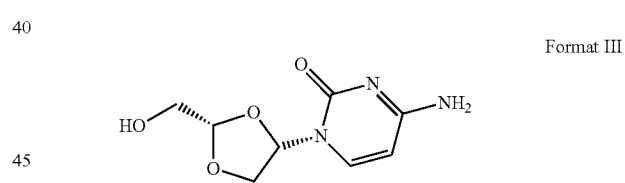

Format III

Highlight 3: this invention provides the crystallization method of crystal form A that includes the following procedures: Heat formula III compound to 80° C. using a baking oven, maintain for 10 min and cool down to room temperature.

Highlight 4: this invention provides the crystal form of monohydrate of formula III compound (crystal form C). The crystal form has a basically identical X-ray powder diffractogram to that shown in the FIG. 4.

Format III

Highlight 5: this invention provides the crystallization method of crystal form C that includes the following procedures: Dissolve formula III compound in water, volatilize in a fume hood with the top open for 3 days, transfer into a vacuum drying oven and volatilize with the top open for 1 day.

Highlight 6: this invention provides the crystal form of formula III compound (crystal form E). The crystal form has a basically identical X-ray powder diffractogram to that shown in the FIG. 7.

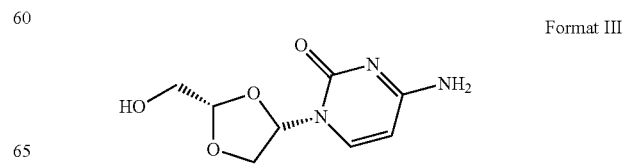

Format III

Highlight 7: this invention provides the crystallization method of crystal form E that includes the following procedures: Add methanol and acetone to formula III compound, with the volume ratio of methanol to acetone being 1:9, mix the suspension for 3 days, and centrifugate for 3 min at a rate of 10000 rpm. Precipitate and vacuum dry for 1 h.

Eighthly, this invention provides solid dosage forms, including crystal forms A, C and/or E, and pharmaceutically accepted excipients.

Highlight 8: this invention provides the use of crystal forms A, C and/or E in preparation of anti-tumor and/or antiviral drugs.

Details of Invention

The synthesis method described in the highlight 1 of this prevention is a new synthesis method of troxacitabine. This method is suitable for commercial production since it is composed of two steps of chemical reaction and corresponding purification methods.

The optimized synthesis method in the highlight 1 includes:

(1) Synthesis: Drop in trimethyliodosilane into mixture formula I compound and dichloromethane at 0±3° C. under the protection of inert gas (preferably nitrogen), mix to react for 2.5±0.5 h, add hexamethyldisilazane and $N^4$-acetylcytosine, and mix to react for 3.5±0.5 h.

Purification: Increase the temperature of the above-mentioned reaction system to 22±3° C., drop in sodium thiosulfate, and add diatomaceous earth. Mix and filtrate. Wash the filter cake, add dichloromethane at 27±3° C., mix and filtrate. Remove the solvent to obtain the solids processed with the cake. Combine the filtrate with the washings of the cake, separate organic phase and dry after washing. Filtrate, remove the solvent from the filtrate and mix the resulted residues with acetone and isopropyl acetate. Heat to reflux, mix and reduce the temperature to 22±3° C. Filtrate, dry and obtain the solids processed with the filtrate. Combine the solids processed with the cake and filtrate, add isopropyl acetate and acetone, and reflux to heat. Mix, reduce the temperature to 22±3° C. and filtrate. Wash and dry to obtain formula II compound;

(2) Synthesis: Combine the formula II compound obtained in the mixing step (1) and methanol, mix, drop in sodium methoxide-methanol solution and sit to react at 22.5±2.5° C. for 5 h;

Purification: Adjust the above-mentioned reaction system to a pH of 6.5±0.5 at 0±3° C., load the sample on to silica gel column, elute and collect the distillate containing formula III compound. Evaporate to dryness, add dehydrated alcohol and mix. Heat to reflux, reduce the temperature to below room temperature and mix for 12±2 h. Further reduce the temperature to 2.5±2.5° C., mix for 4.5±0.5 h and filtrate. Perform suction filtration after cake washing and dry to obtain formula III compound.

For the optimized synthesis method described in the Highlight 1 of this invention, in the synthesis step under Step (1), the weight ratio of formula I compound:dichloromethane:trimethyliodosilane:hexamethyldisilazane:$N^4$-acetylcytosine is 1:18.0:1.5:3.64:1.15;

For the optimized synthesis method described in the Highlight 1 of this invention, in the synthesis step under Step (2), the weight ratio of formula I compound:methanol is 1:0.045.

For the optimized synthesis method described in the Highlight 1 of this invention, in the purification step under Step (2), the eluent for silica gel column is dichloromethane or methanol, with the volume ratio of dichloromethane:methanol preferably being 4:1.

Further optimize the synthesis method described in the Highlight 1 of this invention, including the crystallization step, i.e., repetition of crystallization step after the purification step in the Step (2). The optimized crystallization method is selected from (a), (b) or (c):

(a) Heat the formula III compound in a baking oven to 80° C., maintain for 10 min and cool down to room temperature;

(b) Dissolve formula III compound in water, volatilize in a fume hood with the top open for 3 days, transfer into a vacuum drying oven and volatilize with the top open for 1 day.

(c) Add methanol and acetone to formula III compound, with the volume ratio of methanol to acetone being 1:9, mix the suspension for 3 days, and centrifugate for 3 min at a rate of 10000 rpm. Precipitate and vacuum dry for 1 h.

These crystallization steps are used for the preparation of crystal forms A, C and E.

The crystal form described in the Highlight 2 of this invention, also known as crystal form A in this disclosure, can be prepared using the following crystallization method described in the Highlight 3 of this invention: Heat the formula III compound in a baking oven to 80° C., maintain for 10 min and cool down to room temperature The crystal form described in the Highlight 4 of this invention, also known as crystal form C in this disclosure, is the crystal form of monohydrate of formula III compound. Crystal form C is the most stable crystal form at room temperature and room humidity and poorly hygroscopic, and has good physical and chemical stability as compared with the 7 crystal forms discovered by the originator of this invention, in particular crystal forms A and B. Therefore, crystal form C is the most optimized crystal form in this invention, and can be prepared using the following crystallization method described in the Highlight 5 of this invention: Dissolve formula III compound in water, volatilize in a fume hood with the top open for 3 days, transfer into a vacuum drying oven and volatilize with the top open for 1 day.

The crystal form described in the Highlight 6 of this invention, also known as crystal form E in this disclosure, can be prepared using the following crystallization method described in the Highlight 7 of this invention: Add methanol and acetone to formula III compound, with the volume ratio of methanol to acetone being 1:9, mix the suspension for 3 days, and centrifugate for 3 min at a rate of 10000 rpm. Precipitate and vacuum dry for 1 h.

The solid dosage forms described in the Highlight 8 of this invention include crystal forms A, C and/or E, and optimization includes crystal form C. The pharmaceutically accepted excipients used in this article are nontoxic fillers, stabilizers, disintegrants, solubilizers or other excipients. These excipients are usually in solid form. The technical staff can combine the drugs into various dosage form based on the purpose of treatment and method of administration (e.g. injection or oral administration). The combination in unit dose is preferably selected, such as powder injections, tablets or capsules, and the combinations as powder for injection are more preferably selected.

These solid dosage forms can be used for the treatment and prevention of tumor and/or viral infection, e.g. for the treatment or prevention of liver cancer, and/or for the treatment or prevention of hepatitis B viral infection.

The use of Highlight 9 of this invention can also be converted into the method to treat or prevent tumor and/or viral infection, including administration of effective doses of crystal forms A, C and/or E for the treatment or prevention in individuals, or conversion into crystal forms A, C and/or E for the treatment or prevention of tumor and/or viral infection.

The optimized use of Highlight 9 of this invention is the use of crystal form C.

For the optimized use of Highlight 9 of this invention, the tumor is liver cancer; and/or the virus is hepatitis B virus. To be more specific, for the optimized use of Highlight 9 of this invention, the drugs are solid dosage forms.

The synthesis method of troxacitabine in this invention is associated with high purity of products, which allows for equally proportional scale up and is suitable for commercial production; The crystal forms identified in this invention (in particular crystal form C) is stable and poorly hygroscopic, which is in particular suitable for storage and transport as solid dosage forms.

For better understanding, this invention cited public references with a view to better describing this invention. Their full contexts are included in this article for reference.

This invention will be described below in a detailed manner through specific embodiments and figures. It should be noted that these descriptions are exemplary in nature and does not constitute any restriction on the scope of this invention. As discussed in this package disclosure, many changes and alterations in this invention appear evident to the technical staff in their field.

DETAILS OF IMPLEMENTATION METHOD

Figure 1:
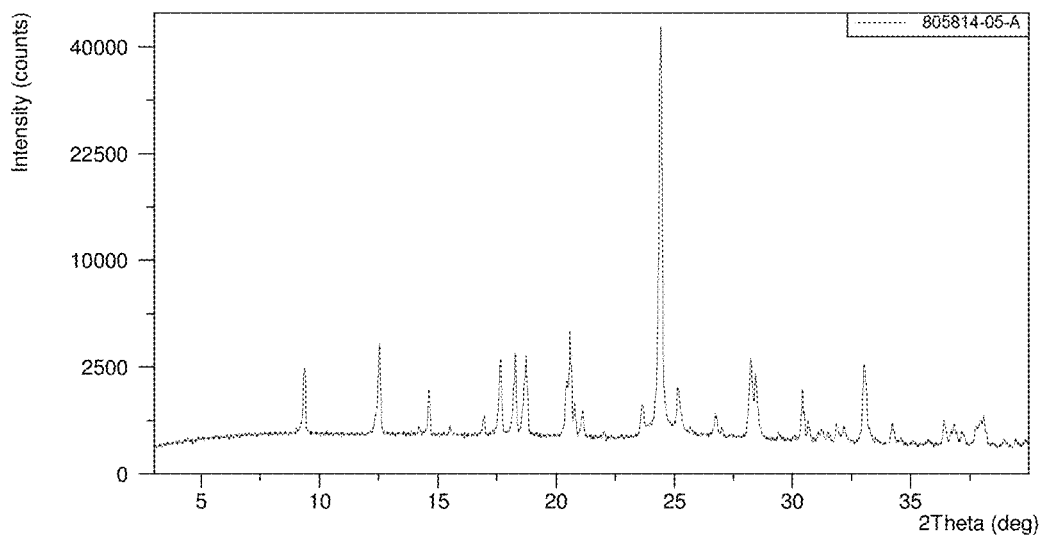
FIGS. 1 to 3 present the superficial characteristic spectra of crystal form A, among which, FIG. 1 displays the XRPD spectrum of crystal form A, FIG. 2 displays the TGA/DSC overlay spectrum of crystal form A, and FIG. 2 displays the 1H NMR spectrum of crystal form A.
Figure 2:
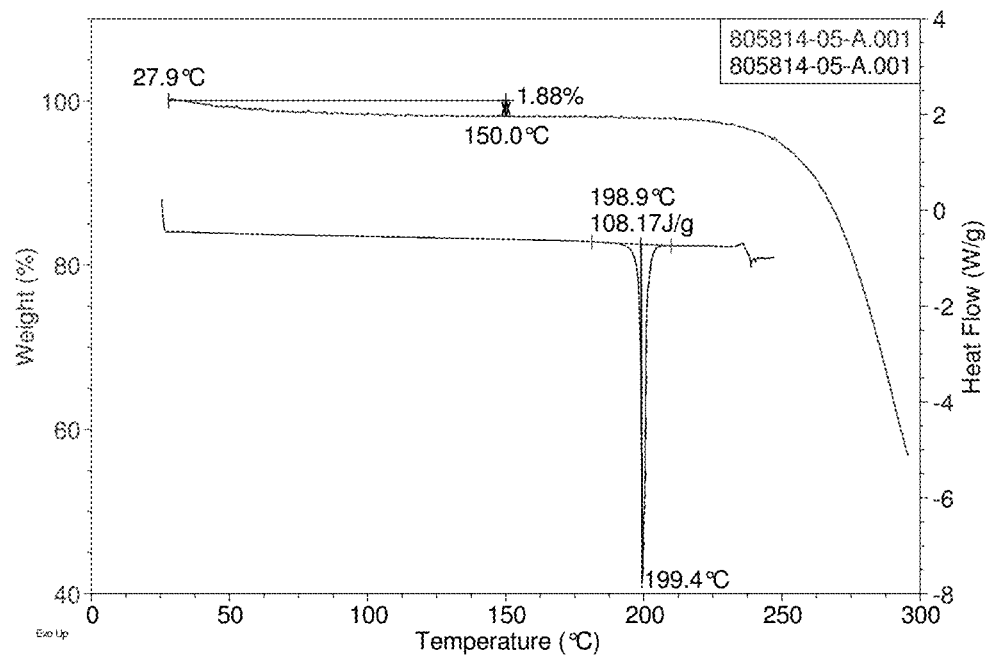
Figure 3:
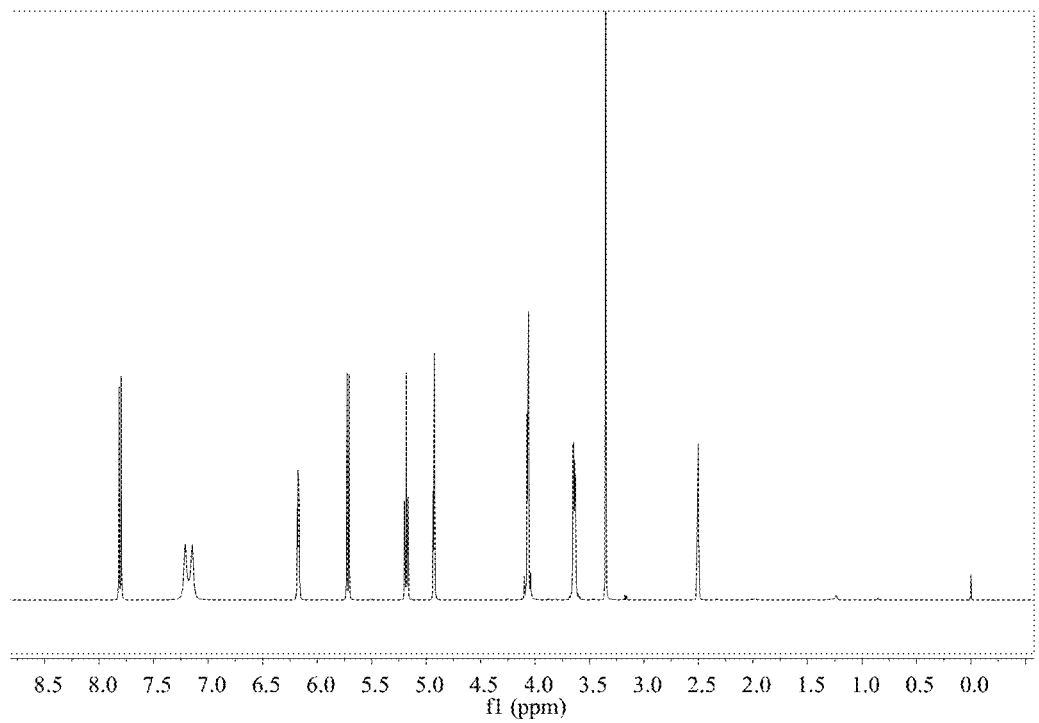
Figure 4:
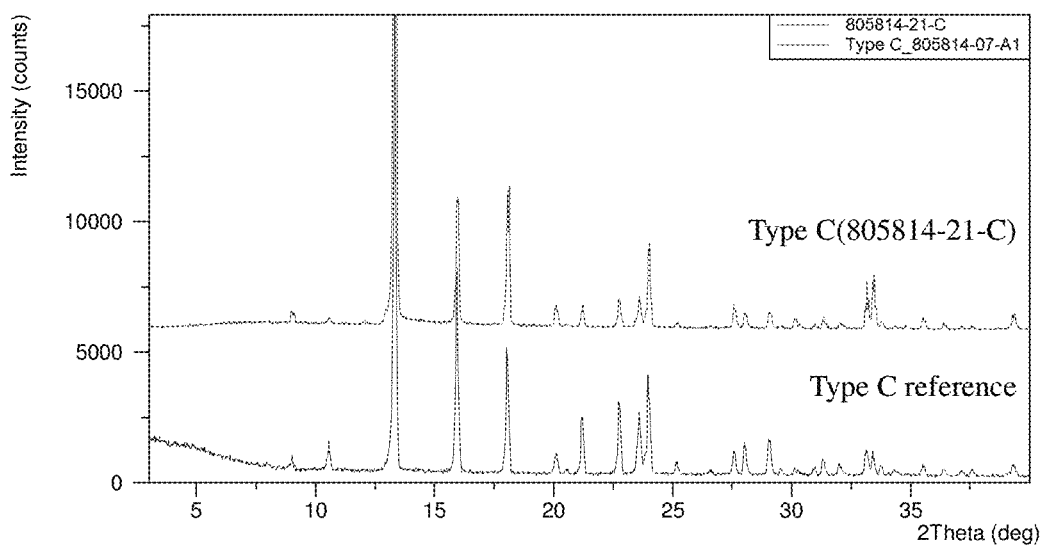
FIGS. 4 to 6 present the superficial characteristic spectra of crystal form C, among which, FIG. 4 displays the XRPD spectrum (the overlay spectrum from two repeated parallel tests) of crystal form C, FIG. 5 displays the TGA/DSC overlay spectrum of crystal form C, and FIG. 6 displays the XRPD overlay spectra of crystal form C (before and after heating) and crystal form A.
Figure 5:
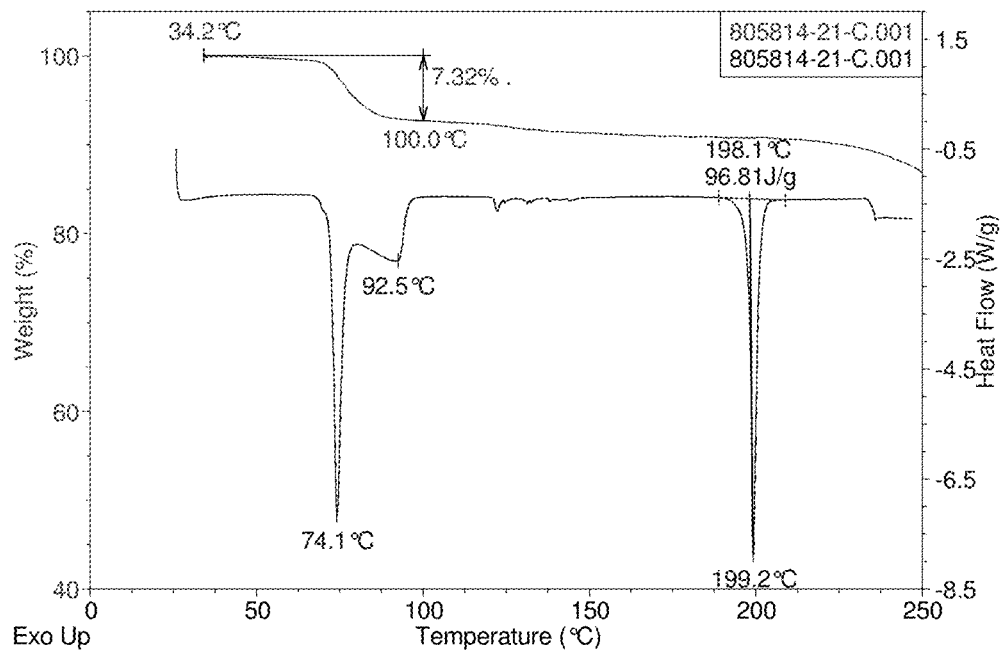
Figure 6:
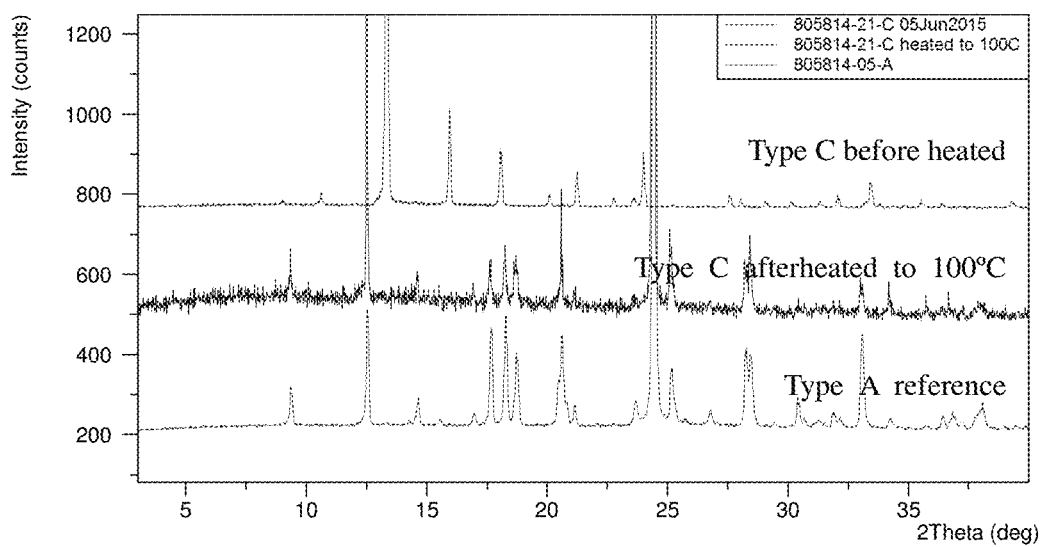
Figure 7:
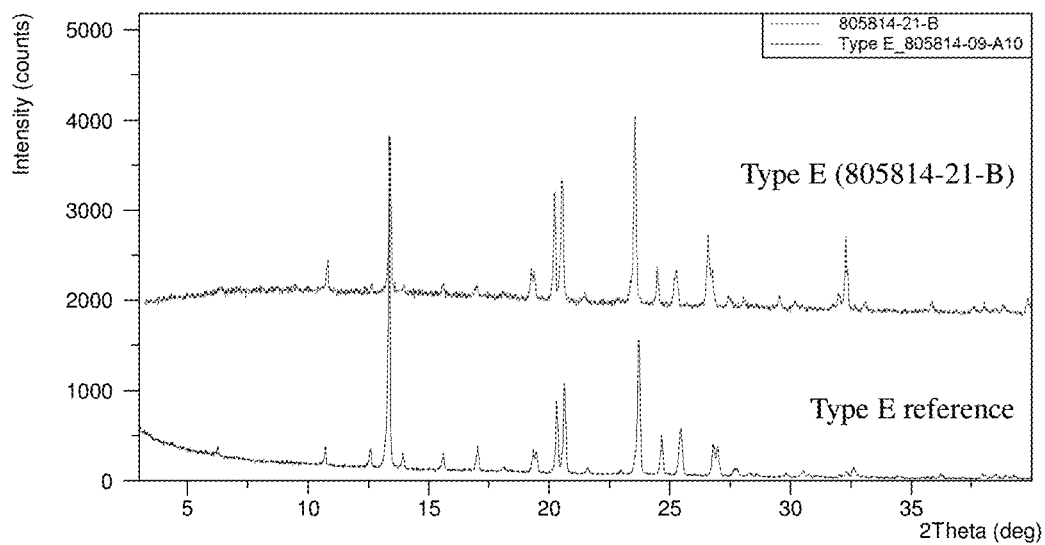
FIGS. 7 to 9 present the superficial characteristic spectra of crystal form E, among which, FIG. 7 displays the XRPD spectrum (the overlay spectrum from two repeated parallel tests) of crystal form E, FIG. 8 displays the XRPD overlay spectra of crystal form E (before and after heating and storage) and crystal forms A and C, and FIG. 9 displays the DSC overlay spectra of crystal form E before and after heating and storage.
Figure 8:
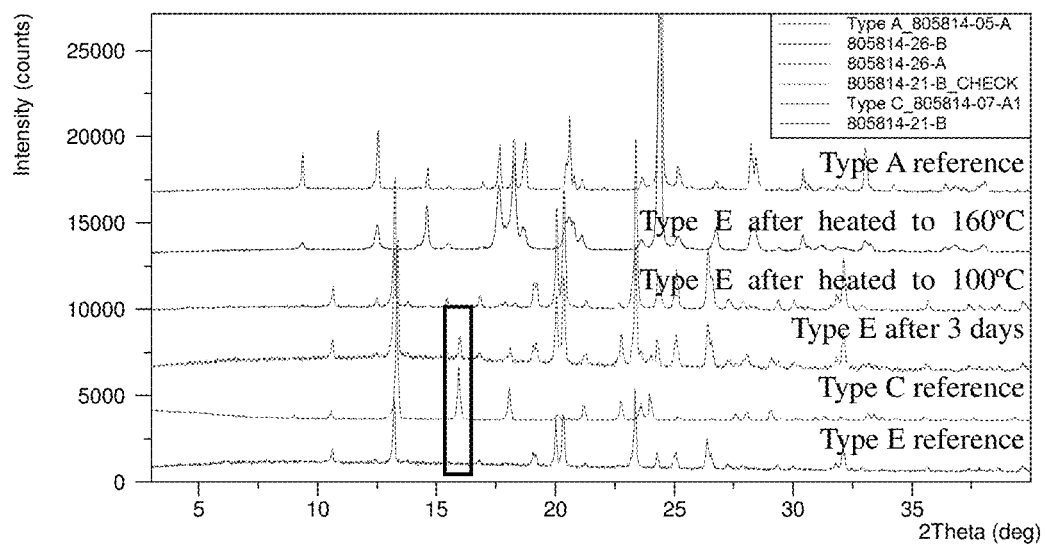
Figure 9:
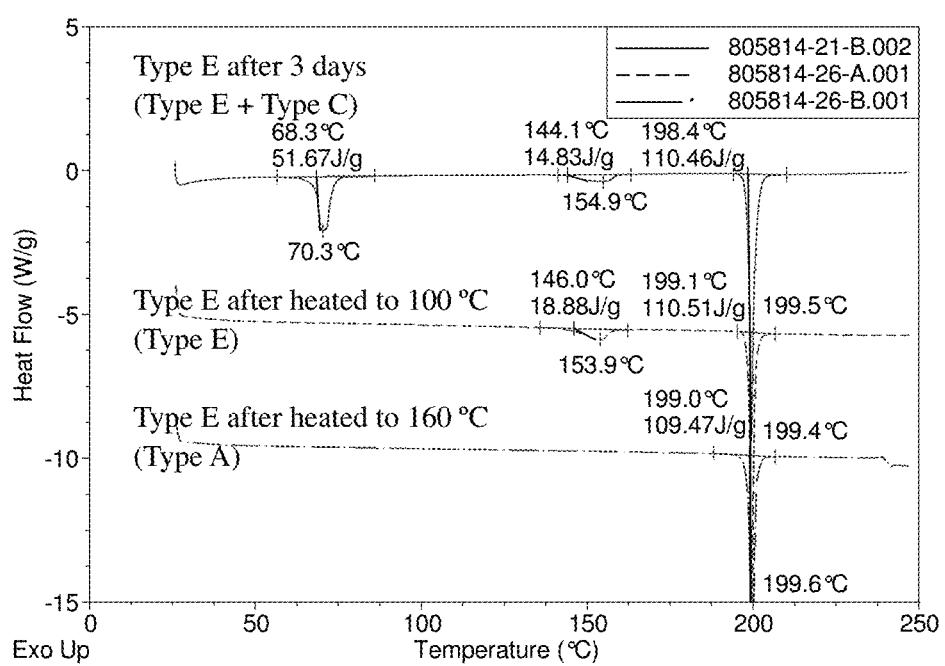

Description is provided below by embodiments.

Embodiment 1 Synthesis of Troxacitabine

The route of synthesis is presented using the reaction formula below:

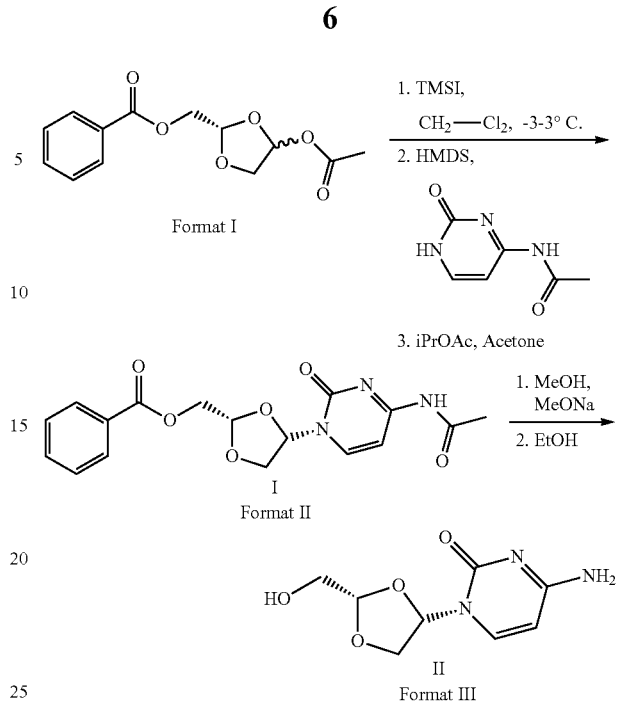

Format I

Format II

Format III

Step 1: Preparation of Formula II

Add in order 18.0 g of dichloromethane and 1 g of formula I to the reaction kettle, cool the internal temperature of the kettle to 0±3° C. under the protection of nitrogen, and slowly drop 1.5 g of trimethyliodosilane. Maintain the internal temperature of the kettle at 0±3° C. and mix under the protection of nitrogen for 2.5±0.5 h until complete reaction is achieved (samples are collected for TLC testing: the ratio of petroleum ether:ethyl acetate as developers=4:1 (v/v), disappearance is obtained at $R_f$=0.5). Continue to maintain the internal temperature of the kettle at 0±3° C. and slowly drop 3.64 g of hexamethyldisilazane and 1.15 g of N4-acetylcytosine. Maintain the internal temperature of the kettle at 0±3° C. after feeding and mix under the protection of nitrogen for 3.5±0.5 h until complete reaction is achieved (samples are collected for TLC testing: the ratio of petroleum ether:ethyl acetate as developers=4:1 (v/v), disappearance is obtained at $R_f$=0.2).

Increase the temperature, maintain the internal temperature of the kettle at 22±3° C. and slowly drop 10%% (w/w) aqueous solution of sodium thiosulfate. Add 0.5 g of diatomaceous earth after the addition of 5 g of aqueous solution of sodium thiosulfate, mix for 1 h and filtrate. Wash 3 times the filter cake with dichloromethane by beating and collect the cake for use. Combine the filtrate and washings into the kettle, separate aqueous phase from organic phase and wash the organic phase with 11.3 g of saturated salt solution once to separate the organic phase. Dry the organic phase with anhydrous overnight to remove the water contained, filtrate sodium fulfate solids and transfer the filtrate to a rotary evaporator. Maintain the evaporator at not more than 45° C. until distillation ends. Transfer the residues obtained from rotary evaporation to the kettle, add 11.2 g of acetone and 18.5 g of isopropyl acetate, and heat to reflux (68±3° C.). Stir into paste and maintain for 1 h. Continue to slowly reduce the inner temperature of the kettle to 22±3° C. within 2.5±0.5 h, rapidly filtrate and vacuum dry the cake in a drying oven at about 40° C. overnight to obtain white solids (coarse product of formula II) for use.

Transfer the diatomaceous earth filter cake obtained from filtration to the kettle, increase the temperature to 27±3° C., and add 18.0 g of dichloromethane. Stir into paste, maintain for 2 h and filtrate the serous fluid and transfer the filtrate to a rotary evaporator. Maintain the evaporator at not more than 45° C. until distillation ends. Transfer both the solids (coarse product of formula II) obtained from rotary evaporation and the white solids obtained for use in last step to the kettle, add 13.3 g of mixed solvents of isopropyl acetate:acetone=3:2 (v/v), and heat to reflux (68±3° C.). Stir into paste and maintain for 1 h. Continue to slowly reduce the inner temperature of the kettle to 22±3° C. within 2.5±0.5 h, rapidly filtrate and vacuum dry the cake in a drying oven at about 40° C. overnight to obtain the refined product of formula II).

Step 2: Preparation and Refining of Formula III

Transfer 1 g of refined product of formula II to a flask with 4 necks, add 5.0 g of methanol, and mix to uniformly disperse the solids. Weigh 0.045 g of sodium methoxide into 0.135 g of methanol and mix to dissolve sodium methoxide. Drop the sodium methoxide-methanol solution into the flask with 4 necks, thermally react at 22.5±2.5° C. for 1 h until complete reaction is achieved (samples are collected for TLC testing: the ratio of dichloromethane:methanol as developers=4:1 (v/v), disappearance is obtained at $R_f$=0.8).

Adjust the system with the glacial acetic acid to a pH of 6.5±0.5 on an ice bath after complete reaction, add 10 g of silica gel 200-300 mesh (which can be purchased from Qingdao Haiyang Chemical Co., Ltd) for sand production and pack the column for column chromatography, where the eluent is dichloromethane:methanol=4:1 (v/v). Collect the distillate containing troxacitabine, rotarily evaporate to dryness, and transfer the solids obtained from rotary evaporation to a flask with 3 necks. Add 3.0 g of anhydrous ethanol, mix for uniform dispersion (suspension), and heat at 78±2° C. to reflux for 0.5 h. Slowly (within 2.5±0.5 h) reduce the temperature to room temperature after reflux and stir at room temperature for 12 h. Further reduce the temperature to 2.5±2.5° C. and thermally stir for 4.5±0.5 h at this temperature. Filtrate, wash once the filter cake with 1.0 g of cold ethanol and thoroughly vacuum filtrate. Discard the filtrate, transfer the cake to a vacuum drying oven and dry to constant weight at 38±2° C. to obtain the refined product of formula III. Test the product for purity using HPLC.

The above-mentioned methods can be proportionally equally scaled up, e.g., directly scaled up about more than 60-180 folds, i.e., 61.7 g to 185.97 g of formula I (other reactants should be proportionally equally increased) produces a purity of 99.3% to 99.8% and a yield of 65 to 85% as tested by HPLC for the final products (refined product of formula III) after scale up, which completely satisfy the needs of commercial production of troxacitabine for pharmaceutical use.

Embodiment 2 Crystal Form of Troxacitabine

The innovator of this invention set up 103 pleiomorphic screening tests using 7 methods, and obtained 7 crystal forms therefrom, i.e., crystal forms A, B, C, E, F, J and K. Among those, crystal forms B, F and J are instable at common temperature while crystal form K is a crystal form of troxacitabine acetic acid solvate or acetate, crystal form C is a crystal form of troxacitabine monohydrate, and crystal forms A and E are the crystal forms of troxacitabine itself (anhydrous substance).

I. Crystal Form A

Transfer 300.5 mg of the final product obtained in the embodiment 1 to a 5-ml flasket, heat on a baking oven to 80° C. and maintain for 10 min, and cool down to room temperature. The resulted crystal form is called crystal form A and its superficial characteristics are obtained using x-ray powder diffraction (XRPD), thermogravimetric analysis (TGA), differential scanning calorimetry (DSC) and 1H nuclear magnetic resonance spectra (1H liquid NMR). See FIGS. 1 to 3 for results, among which, FIG. 1 displays the XRPD spectrum of crystal form A, FIG. 2 displays the TGA/DSC overlay spectrum of crystal form A (where the samples produce a weight loss of 1.9% when heated to 150° C. and a melting point of 198.9° C. (starting temperature), which demonstrates that crystal form A is an anhydrous crystal form) and FIG. 3 displays the 1H NMR spectrum of crystal form A.

II. Crystal Form C

Transfer 201.3 mg of the final product obtained in the embodiment 1 to a 5-ml flasket, add 0.8 mL of water to dissolve and volatilize in a fume hood with the top open for 3 days. Transfer into a vacuum drying oven (<−100 KPa) and volatilize with the top open for 1 day. The resulted crystal form is called crystal form C and its superficial characteristics are obtained using x-ray powder diffraction (XRPD), thermogravimetric analysis (TGA) and differential scanning calorimetry (DSC). See FIGS. 4 to 6 for results, among which, FIG. 4 displays the XRPD spectrum of crystal form C (the overlay spectrum from two repeated parallel tests) that shows good stability in the position of all peaks, FIG. 5 displays the TGA/DSC overlay spectrum of crystal form C (where the samples produce a weight loss of 7.3% when heated to 100° C. (the theatrical weight loss is 7.8% for monohydrates) and three endothermic peaks are observed at 74.1° C. (peak temperature), 92.5° C. (peak temperature) and 198.1° C. (starting temperature)), and FIG. 6 displays the XRPD spectra (overlay) of crystal form C before and after heating and crystal form A (where conversion of crystal form C into crystal form A when heated to 100° C. and a TGA weight loss of 7.3% demonstrate that crystal form C is a monohydrate).

II. Crystal form E

Transfer 199.8 mg of the final product obtained in the embodiment 1 to a 5-ml flasket, add 4.0 mL of methanol: acetone=1:9 (v/v), and mix the suspension for 3 days. Centrifugate for 3 min at a rate of 10000 rpm, precipitate and vacuum dry for 1 h. The resulted crystal form is called crystal form E and its superficial characteristics are obtained using x-ray powder diffraction (XRPD) and differential scanning calorimetry (DSC). See FIGS. 7 to 9 for results, among which, FIG. 7 displays the XRPD spectrum of crystal form E (the overlay spectrum from two repeated parallel tests) that shows good stability in the position of all peaks, FIG. 8 displays the XRPD spectra (overlay) of crystal form E before and after heating and storage and crystal forms A and C (the XRPD spectrum from the samples of crystal form E that have been stored for 3 months shows diffraction peak of crystal form C, which indicated crystal form E has a tendency to convert into crystal form C after being stored in air. The diffraction peak of crystal form C disappears on the XRPD spectrum when heated to 100° C. The XRPD spectrum demonstrates conversion of crystal form E into crystal form A when heated to 160° C.), and FIG. 9 displays the DSC spectra (overlay) of crystal form E before and after heating and storage (where three endothermic peaks are observed on the DSC spectrum of the samples of crystal form E after being stored for 3 days, which shows the presence of mixture of crystal forms C and E. The first endothermic peak disappears from the DSC spectrum when heated to 100° C. (the first endothermic peak at a starting temperature of 68.3° C. is the dehydration peak of crystal form C), the second endothermic peak disappears from DSC spectrum when heated to 160° C., that is, the second endothermic peak at a starting temperature of 146.0° C. is the crystal form conversion peak of crystal form A from crystal form E.)

Embodiment 3 Study of the Nature of Crystal Forms A, C and E of Troxacitabine

The innovator of this invention have found that the samples of crystal form A will partially convert into crystal form C after 1-month storage, and thereby begun to further study these crystal forms.

I. Hygroscopicity Study

The hygroscopicity of crystal forms A, C and E is evaluated by DVS method at 25° C. Crystal form A begins to absorb water at 70% RH and absorbs 8.4% of water at 90% RH. The XRPD spectrum shows that it begins to convert into crystal form C after water absorption. Crystal form E begins to absorb water at 80% RH and absorbs 8.5% of water at 90% RH. The XRPD spectrum shows that it begins to convert into crystal form C after water absorption. Crystal form C has a hygroscopicity of 0.14% at 25° C./80% RH and is difficult to be eliminated at a low humidity, which shows that the crystal water in crystal form C is strongly bound. The XRPD spectrum shows crystal form C remain the same in crystal form before and after DVS. Therefore, hydrate crystal form C is deemed as the most stable crystal form at room temperature and room humidity. Therefore, crystal form C is selected for further stability study.

II. Stability Study

Crystal form C is evaluated for its physical-chemical stability when placed at 80° C. for 24 h (with the top closed) as well as at 40° C./75% RH and 25° C./60% RH for 1 week (with the top open). The chemical and physical stability of the samples are tested by XRPD, TGA, DSC and HPLC. The test results are presented in Table 1, which demonstrate that crystal form C is physically stable at 40° C./75% RH and 25° C./60% RH (common temperature conditions for drug transport). The chemical impurity analysis shows troxacitabine remain unchanged under these 3 conditions, which supports crystal form C is chemically stable.

TABLE 1

Data on stability study of crystal form C

| Time point | Conditions | Crystal form | TGA weight loss (heated to 100° C.) | DSC endothermic peak (peak temperature) | Impurity (area %) |
|---|---|---|---|---|---|
| 0 h | NA | Crystal form C | 8.0 | 69.4, 93.3, 198.3* | 100.0 |
| 24 h | 80° C. | Crystal form A | 0.4 | 199.2* | 100.0 |
| 1 week | 25° C./ 60% RH | Crystal form C | 8.2 | 69.4, 96.7, 198.9* | 100.0 |
| 1 week | 40° C./ 75% RH | Crystal form C | 7.9 | 70.1, 88.4, 198.8* | 100.0 |

*Starting temperature.

The invention claimed is:

1. Synthesis method for Formula III compound, comprising a synthesis reaction formula as shown below:

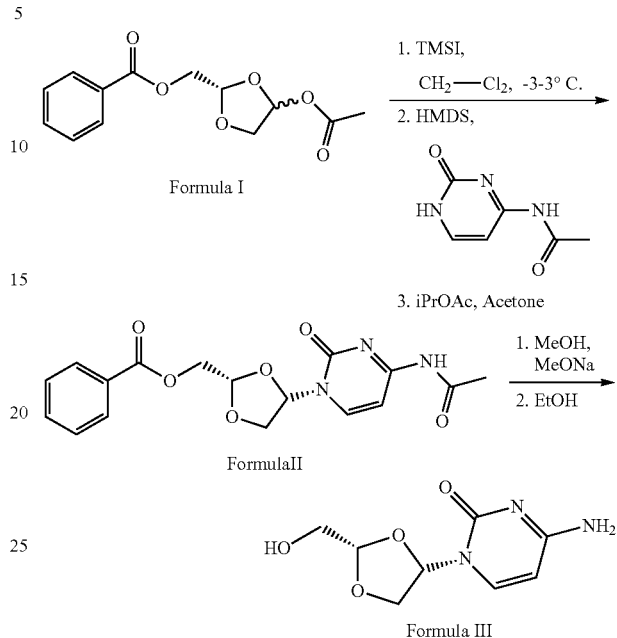

wherein Formula I is a starting composition, Formula II is an intermediate composition, and Formula III is the Formula III compound, and wherein the method comprises the steps of:
a first synthesis step wherein trimethyliodosilane is dropped into a mixture of a Formula I compound and dichloromethane at 0±3° C. under protection of inert gas, mixed to react for 2.5±0.5 h, then hexamethyldisilazane and N[4]-acetylcytosine is added, and mixed to react for 3.5±0.5 h and produce a first reaction system;
a first purification step wherein temperature of the first reaction system is increased to 22±3° C., sodium thiosulfate is dropped in, and diatomaceous earth is added, followed by mixing and filtration to produce a filter cake and a filtrate;
washing the filter cake, adding dichloromethane at 27±3° C., followed by mixing and filtration to produce a first solid and a first solvent;
separating the first solvent from the first solid;
combining the filtrate and the first solvent to form a mixture;
separating an organic phase from the mixture and drying after washing;
removing solvent from the filtrate to obtain residues; and
mixing the residues with acetone and isopropyl acetate to make a residue mixture;
heating the residue mixture to reflux, mixing and reducing temperature to 22±3° C. to provide a reduced temperature mixture;
filtrating the reduced temperature mixture, drying and obtaining a second solid;
combining the first solid and the second solid to form a solids mixture;
adding isopropyl acetate and acetone to the solids mixture, and refluxing to heat;

mixing, reducing the temperature to 22±3° C. and
filtrating to obtain a further solid; washing and
drying the further solid to obtain a Formula II
compound;
a second synthesis step wherein the Formula II compound and methanol are combined, mixed, dropped
in sodium methoxide-methanol solution and sit to
react at 22.5±2.5° C. for 5 h to produce a second
reaction system;
a second purification step wherein the second reaction
system is adjusted to a pH of 6.5±0.5 at 0±3° C.,
loaded on to a silica gel column, and eluted, and a
liquid is collected which contains a produced Formula III compound;
evaporating the liquid to dryness, adding dehydrated
alcohol and mixing;
heating to reflux, reducing temperature to below room
temperature and mixing for 12±2 h;
further reducing temperature to 2.5±2.5° C., mixing for
4.5±0.5 h and filtrating to obtain a further filter cake;
performing suction filtration of the further filter cake
and drying to obtain the Formula III compound; and
further including at least one crystallization step
selected from the group consisting of:
(a) heat the Formula III compound on a baking oven
to 80° C., maintain for 10 min and cool down to
room temperature;
(b) dissolve the Formula III compound in water,
volatilize in a fume hood with top open for 3 days,
transfer into a vacuum drying oven and volatilize
with top open for 1 day; and
(c) add methanol and acetone to the Formula III compound, with volume ratio of methanol to acetone being
1:9, mix the suspension for 3 days, and centrifuge for
3 min at a rate of 10000 rpm, and precipitate and
vacuum dry for 1 h.

2. The method as specified in claim 1, wherein, in the first synthesis step, weight ratio of the Formula I compound:dichloromethane:trimethyliodosilane:hexamethyldisilazane:$N^4$-acetylcytosine is 1:18.0:1.5:3.64:1.15.

3. The method as specified in claim 1, wherein, in the second purification step, the eluent for the silica gel column is dichloromethane, methanol or a mixture thereof, with a volume ratio of dichloromethane:methanol being 4:1.

4. The method as specified in claim 1, wherein, in the first synthesis step, weight ratio of formula I compound:dichloromethane:trimethyliodosilane:hexamethyldisilazane:$N^4$-acetylcytosine is 1:18.0:1.5:3.64:1.15; and/or wherein, in the second synthesis step, weight ratio of formula II compound:methanol is 1:0.045.

5. The method of claim 1, wherein the sodium thiosulfate is added as an aqueous solution.

6. Synthesis method for Formula III compound, comprising a synthesis reaction formula as shown below:

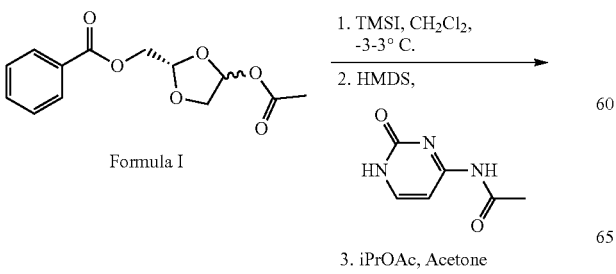

Formula I

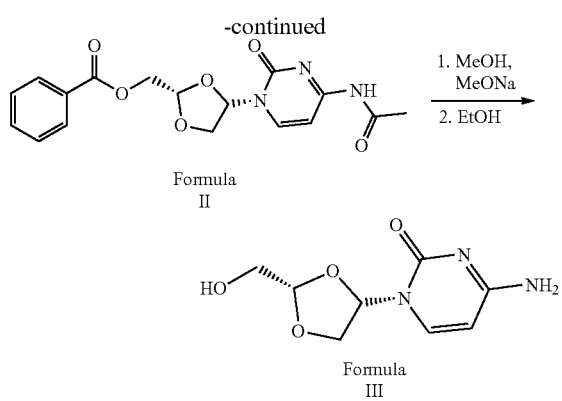

Formula II

Formula III wherein Formula I is a starting composition, Formula II is
an intermediate composition, and Formula III is the
Formula III compound, and wherein the method comprises the steps of:
a first synthesis step wherein trimethyliodosilane is
dropped into a mixture of a Formula I compound and
dichloromethane at 0±3° C. under protection of inert
gas, mixed to react for 2.5±0.5 h, then hexamethyldisilazane and $N^4$-acetylcytosine is added, and
mixed to react for 3.5±0.5 h and produce a first
reaction system;
a first purification step wherein temperature of the first
reaction system is increased to 22±3° C., sodium
thiosulfate is dropped in, and diatomaceous earth is
added, followed by mixing and filtration to produce
a filter cake and a filtrate;
washing the filter cake, adding dichloromethane at
27±3° C., followed by mixing and filtration to produce a first solid and a first solvent;
separating the first solvent from the first solid;
combining the filtrate and the first solvent to form a
mixture;
separating an organic phase from the mixture and
drying after washing;
removing solvent from the filtrate to obtain residues;
and
mixing the residues with acetone and isopropyl acetate
to make a residue mixture;
heating the residue mixture to reflux, mixing and reducing temperature to 22±3° C. to provide a reduced
temperature mixture;
filtrating the reduced temperature mixture, drying and
obtaining a second solid;
combining the first solid and the second solid to form
a solids mixture;
adding isopropyl acetate and acetone to the solids
mixture, and refluxing to heat;
mixing, reducing the temperature to 22±3° C. and
filtrating to obtain a further solid; washing and
drying the further solid to obtain a Formula II
compound;
a second synthesis step wherein the Formula II compound and methanol are combined, mixed, dropped
in sodium methoxide-methanol solution and sit to
react at 22.5±2.5° C. for 5 h to produce a second
reaction system;
a second purification step wherein the second reaction
system is adjusted to a pH of 6.5±0.5 at 0±3° C.,
loaded on to a silica gel column, and eluted, and a
liquid is collected which contains a produced Formula III compound;

evaporating the liquid to dryness, adding dehydrated alcohol and mixing;

heating to reflux, reducing temperature to below room temperature and mixing for 12±2 h;

further reducing temperature to 2.5±2.5° C., mixing for 4.5±0.5 h and filtrating to obtain a further filter cake;

performing suction filtration of the further filter cake and drying to obtain the Formula III compound, wherein, in the second synthesis step, weight ratio of the Formula II compound:methanol is 1:0.045.

7. The method as specified in claim 6, further including at least one crystallization step selected from the group consisting of:
   (a) heat the Formula III compound on a baking oven to 80° C., maintain for 10 min and cool down to room temperature;
   (b) dissolve the Formula III compound in water, volatilize in a fume hood with top open for 3 days, transfer into a vacuum drying oven and volatilize with top open for 1 day; and
   (c) add methanol and acetone to the Formula III compound, with volume ratio of methanol to acetone being 1:9, mix the suspension for 3 days, and centrifugate for 3 min at a rate of 10000 rpm, and precipitate and vacuum dry for 1 h.

8. The method as specified in claim 6, wherein, in the first synthesis step, weight ratio of formula I compound:dichloromethane:trimethyliodosilane:hexamethyldisilazane:$N^4$-acetylcytosine is 1:18.0:1.5:3.64:1.15; and/or wherein, in the second synthesis step, weight ratio of formula II compound:methanol is 1:0.045.

\* \* \* \* \*